United States Patent [19]

Koga

[11] 4,406,015

[45] Sep. 20, 1983

[54] FLUORESCENT X-RAY FILM THICKNESS GAUGE

[75] Inventor: Toshiyuki Koga, Tokyo, Japan

[73] Assignee: Kabushiki Kaisha Daini Seikosha, Tokyo, Japan

[21] Appl. No.: 258,518

[22] Filed: Apr. 28, 1981

[30] Foreign Application Priority Data

Sep. 22, 1980 [JP] Japan ................................ 55-135058

[51] Int. Cl.³ ........................ G01N 23/20; G21K 1/00
[52] U.S. Cl. ..................................... 378/050; 378/89; 378/206
[58] Field of Search ....................... 378/44, 45, 86, 88, 378/206, 50, 89; 250/491.1

[56] References Cited

U.S. PATENT DOCUMENTS

| 2,455,928 | 12/1948 | Hawks | 378/206 |
| 3,705,305 | 12/1972 | Fischer | 378/206 |
| 4,178,513 | 12/1979 | Dubois | 378/44 |
| 4,195,229 | 3/1980 | Suzuki | 378/160 |

Primary Examiner—Alfred E. Smith
Assistant Examiner—T. N. Grigsby
Attorney, Agent, or Firm—Robert E. Burns; Emmanuel J. Lobato; Bruce L. Adams

[57] ABSTRACT

A thickness measuring apparatus in which a shutter is horizontally interposed between an X-ray tube and the collimator defining the irradiated area of the test piece. While the X-ray beam is thus blocked, the area of the test piece which will be irradiated is viewable, via a mirror, thru a microscope. Typically, the device is used for measuring nickel plating on a copper base for which use it is equipped with a cobalt filter.

5 Claims, 16 Drawing Figures

FLUORESCENT X-RAY FILM THICKNESS GAUGE

BACKGROUND OF THE INVENTION

The present invention relates to a fluorescent X-ray film thickness gauge, and more particularly to an improvement of irradiating an X-ray to a sample accurately and of improving detection efficiency by coinciding an X-ray axis with an optical axis of a viewing means.

In the conventional fluorescent X-ray film thickness gauge of this type, when a measuring point "P" on a sample 1 is irradiated by an incident X-ray beam 3 from an X-ray tube 2 positioned above the sample 1 as shown in a principle diagram in FIG. 1, a fluorescent X-ray 4 is emitted from the measuring point "P" to a detector 5 which measures the amount of fluorescent X-rays. On this occasion, the point to irradiate an X-ray is determined by viewing the sample 1 by a microscope and projector as viewing means 6 positioned above the sample. However, since an optical axis 7 of the viewing means 6 does not coincide with the X-ray axis 3 of the X-ray tube 2, i.e. since the surface of the sample 1 is not irradiated at a right angle but at an inclined angle against the X-ray axis 3, the shape of the irradiating point of the X-ray on the sample 1 is not circular but elliptic as indicated by a dotted line in FIG. 2. For instance, when the plating film thickness of very small plating areas provided on an exceedingly precise member such as an IC circuit is measured, the shape of the irradiating point is elliptic even if the X-ray beam is thinned, and the neighboring portions are also irradiated unnecessarily. As a result, the film thickness cannot be measured accurately. Further, if the sample 1 travels vertically, the shape of the irradiating point becomes elliptic and the irradiating position moves, so the measuring accuracy is exceedingly bad condition.

Accordingly, it is an object of the present invention to provide an exceedingly effective method of eliminating the abovementioned drawbacks and make an accurate positioning of X-ray irradiating point by coinciding an X-ray axis from an X-ray tube with an optical axis of a viewing means.

BRIEF DESCRIPTION OF THE DRAWINGS

FIGS. 1 and 2 show the conventional fluorescent X-ray film thickness gauge, in which FIG. 1 shows a whole construction and FIG. 2 shows a flat plan view of X-ray beam which is irradiated on a sample.

Hereinafter the preferred embodiment of the fluorescent X-ray film thickness gauge according to the present invention will be illustrated in conjunction with the accompanying drawings.

Figure 5:
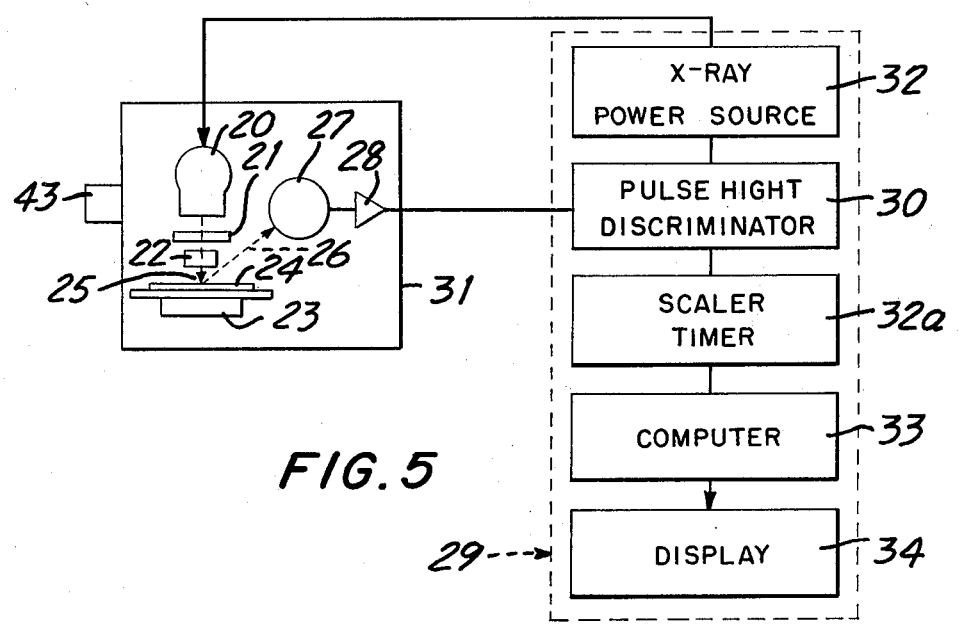
FIG. 5 shows a whole construction of a fluorescent X-ray film thickness gauge of the present invention.

FIG. 5 shows a principle diagram showing an overall structure of a fluorescent X-ray film thickness gauge. Reference numeral 20 denotes an X-ray tube provided with a shutter 21 and a collimator 22 at the lower portion thereof. A sample 24 is positioned on a sample holder 23 below the collimator 22.

The sample 24 is irradiated by an X-ray 25 from the X-ray tube 20, and a fluorescent X-ray 26 emitted from the sample 24 is fed to a detector 27, and converted into an electrical signal by the detector 27 and fed to a pulse height discriminator 30 of a controller 29 by way of an amplifier 28. The controller 29 controls and operates a measuring head 31. A high voltage power source of an X-ray power source 32 is supplied to the X-ray tube 20. An output signal from the pulse hight discriminator 30 are fed to a scaler timer 32a, micro computer 33 and a digital display 34 to display data.

Figure 1:
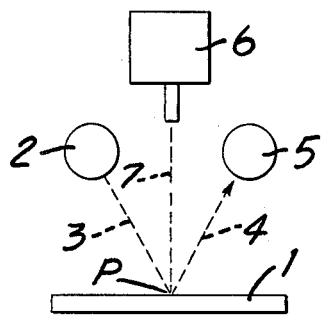
Figure 3:
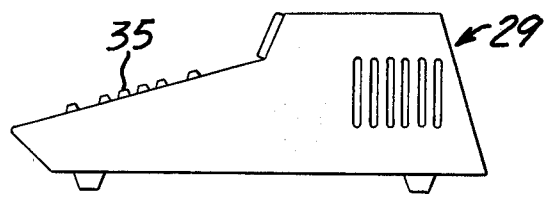
FIG. 3 shows a side view of operation box for a fluorescent X-ray film thickness gauge of the present invention.
Figure 2:
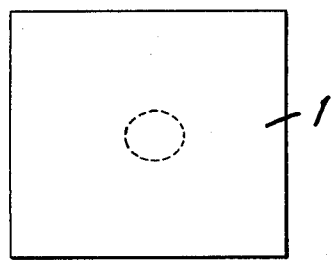
Figure 4:
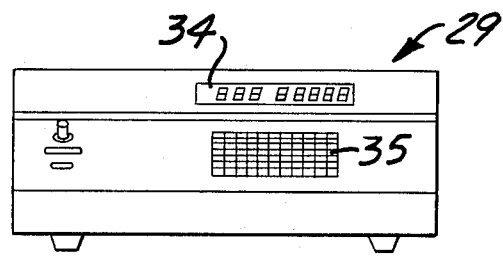
FIG. 4 shows a front view of FIG. 3.
Figure 6:
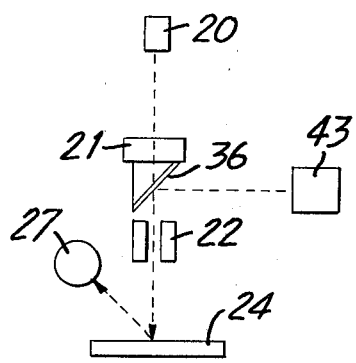
FIG. 6 shows a principle construction of a main part of FIG. 5.
Figure 7:
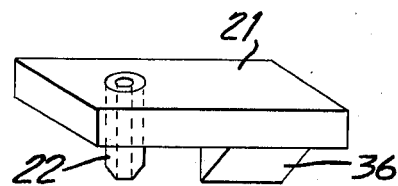
FIG. 7 shows a perspective view of an essential portion of FIG. 6.
Figure 11:
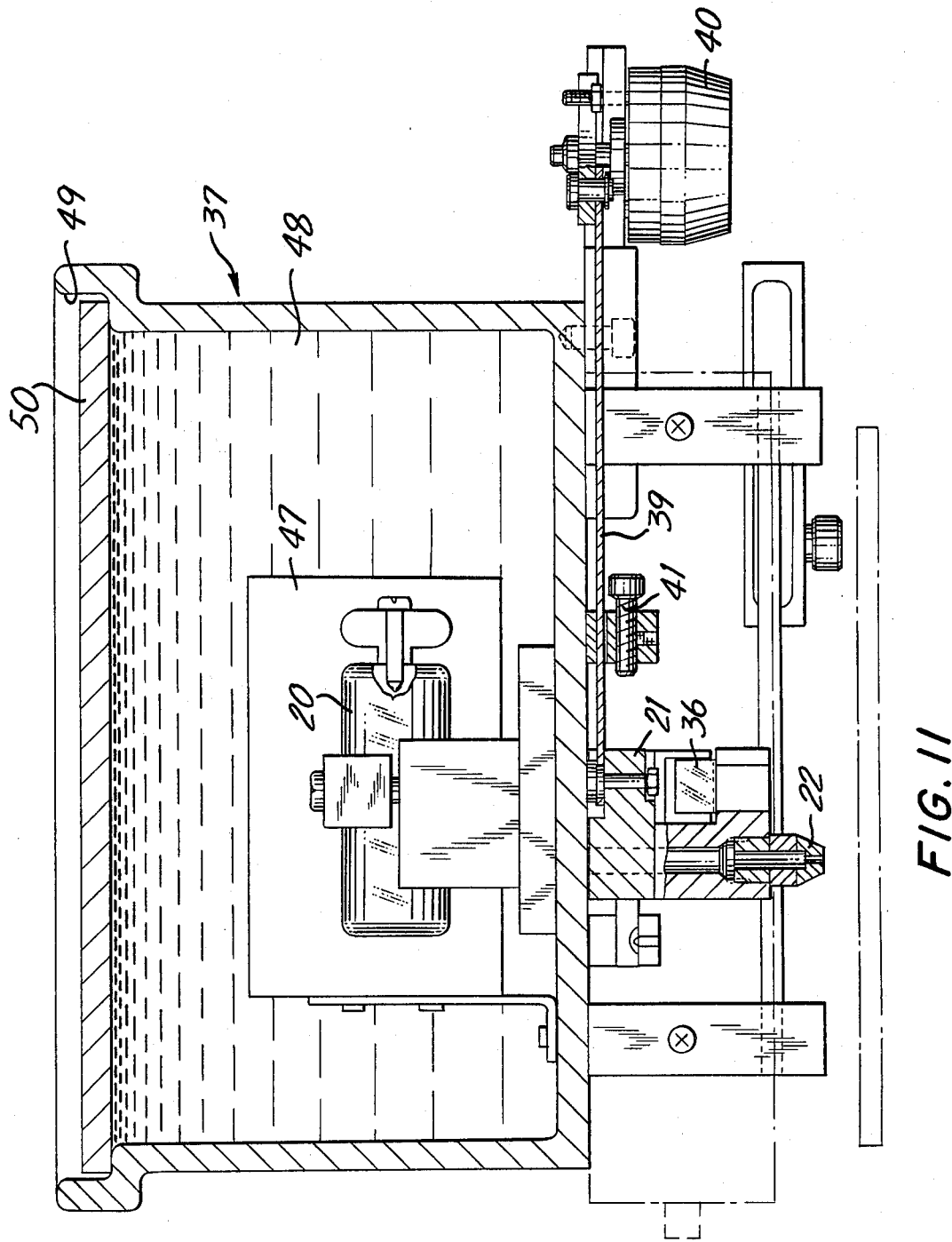
FIG. 11 shows a cross sectional view taken on line A—A of FIG. 10.
Figure 12:
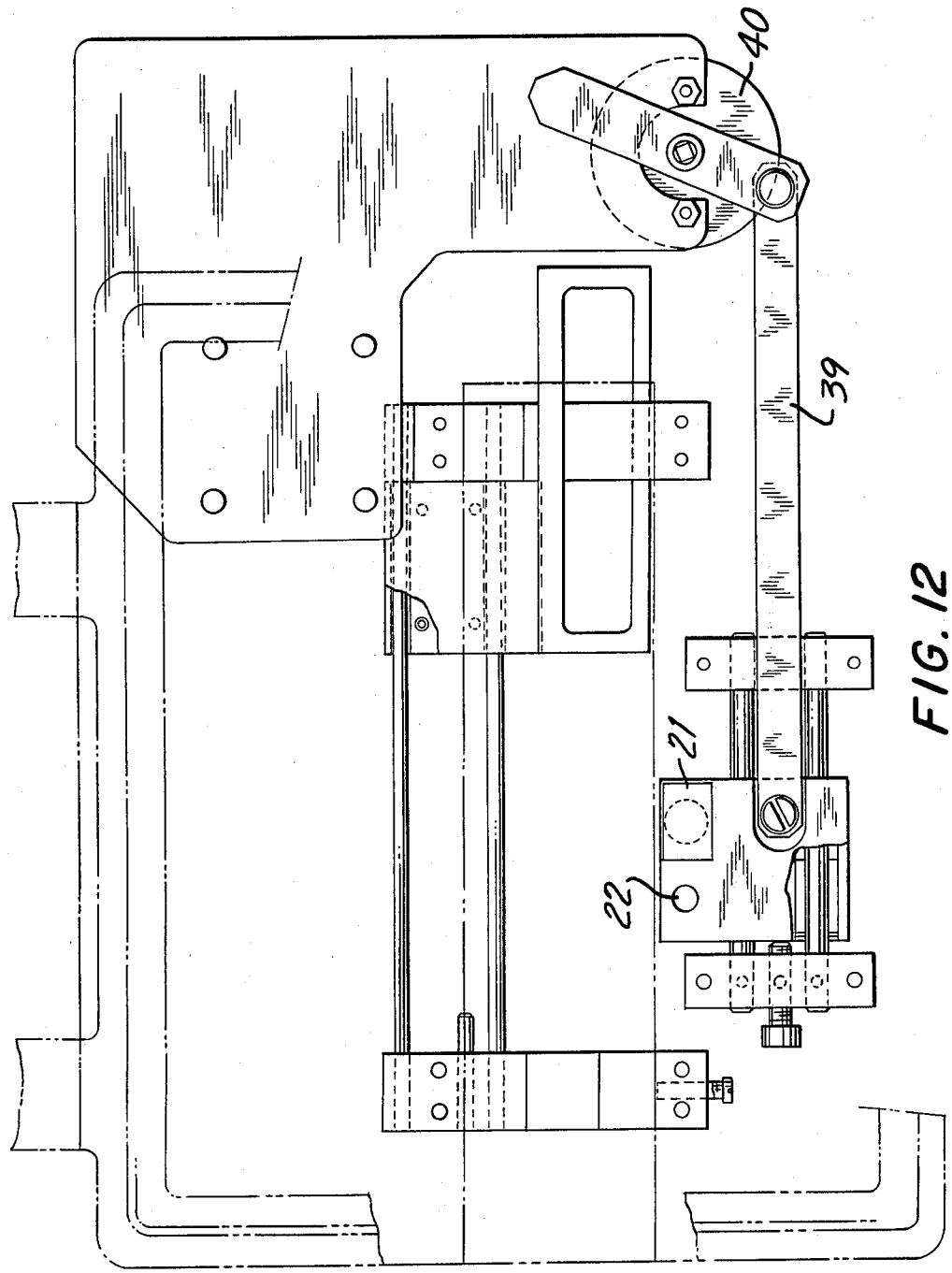
FIG. 12 shows a flat plan view of a main part in FIG. 10.
Figure 13:
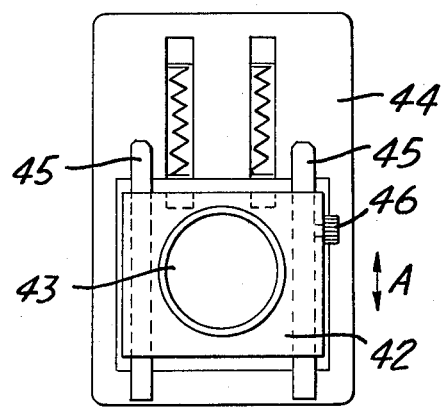
FIG. 13 shows a cross sectional view taken on line B—B of FIG. 10, FIGS. 14 and 15 show a principle construction and perspective view of detector with filter.
Figure 14:
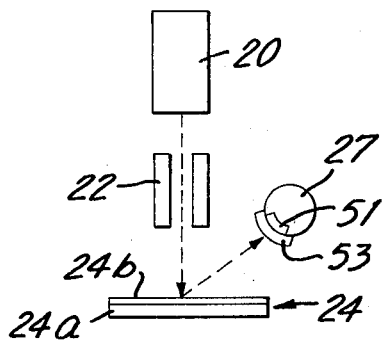
Figure 15:
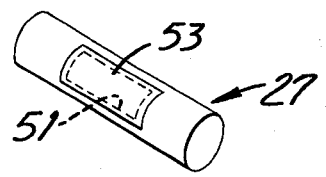
Figure 16:
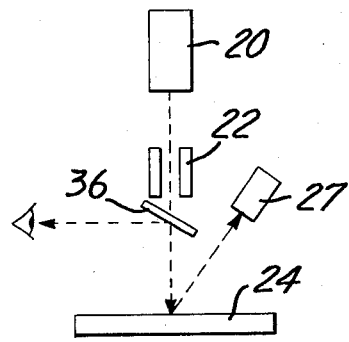
FIG. 16 shows a principle construction of another embodiment.

The controller 29 is constructed as shown in FIGS. 3 and 4, and each data is fed by a key board portion 35. The shutter 21 set at the lower portion of the X-ray tube 20 is provided with a mirror 36 at one end thereof as shown in the principle diagram in FIG. 6. The shutter 21 slides in the horizontal direction as shown in FIGS. 7, 11 and 12, and the collimator 22 is formed in one body with the shutter 21 at the lower portion thereof as shown in FIGS. 6, 7 and 11. The shutter 21 is guided to a guide rail 38 provided at the bottom portion of a tank 37, and a guide plate 39 of the shutter 21 is slided horizontally by a rotary solenoid 40 fixed at the bottom portion of the tank 37, and the shutter 21 is slidably set. The shutter 21 is butted against a stopper screw 41 to control the projection of the screw, whereby the position of the shutter in the horizontal direction is determined. Accordingly, the sample 24 is not irradiated by the X-ray from the X-ray tube 20 shut out by the shutter 21 when the shutter is closed, i.e. when the shutter is under the condition as shown in FIG. 7. The sample 24 is irradiated by the X-ray by way of the collimator when the shutter 21 is slided by the rotary solenoid 40. A holder 42 set at the side wall portion of the tank 37 is provided with a microscope 43 as a viewing means. When the shutter 21 is under the condition as shown in FIG. 7, the upper surface of the sample 24 is viewed through the mirror 36. The holder 42 is set at guide shafts 45 formed on a base plate 44 at the side of the tank 37 slidably in the direction of an arrow mark "A" and positioned at an arbitrary position in the direction of the arrow mark "A" by an adjusting screw 46 as shown in FIG. 13. So the X-ray axis of the X-ray tube 20 coincide with the optical axis of the microscope 43. The X-ray tube 20 set inside the tank 37 is provided with a high voltage power source 47, and the tank 37 is filled with an insulating oil 48, and a cover plate 50 is mounted on an upper opening 49 of the tank 37. The detector 27 is set at the lower portion of the tank 37, and a filter 53 with a filter guide 52 is set at the lower portion of the tank 37 facing an opening 51 of the detector 27. The filter 53 made of cobalt eliminates a fluorescent X-ray of copper and passes a fluorescent X-ray of a nickel spectrum to guide into the detector 27 and counts the amount of the nickel spectrum out of the fluorescent X-rays emitted from the sample 24 as shown in FIGS. 14 and 15. So the film thickness of a nickel plate 24b on a copper base 24a is measured by the amount of the fluorescent X-ray counted by the detector 27.

Figure 8:
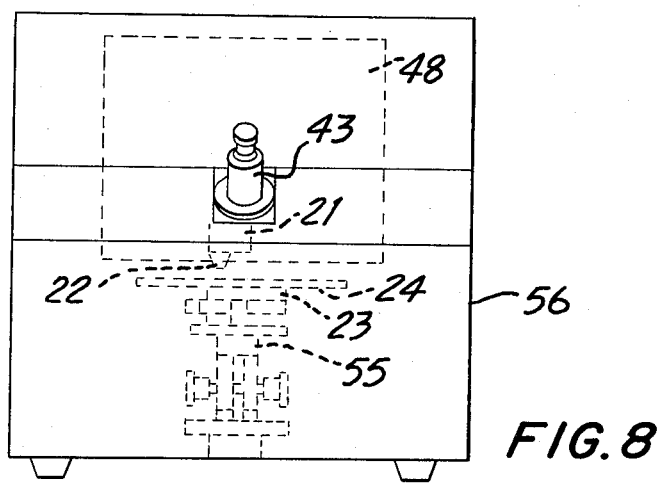
FIG. 8 shows a front view of a fluorescent X-ray film thickness gauge of the present invention.
Figure 9:
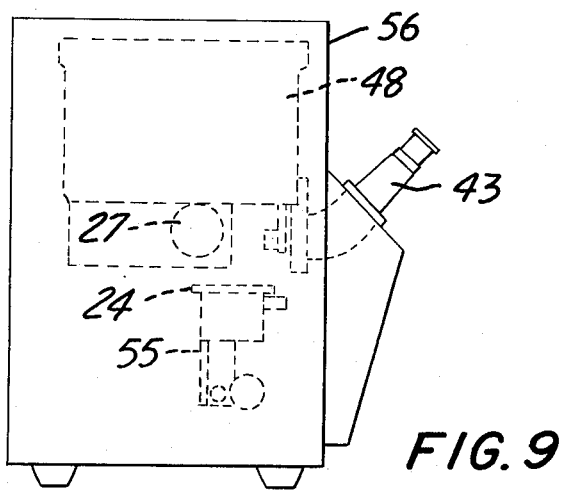
FIG. 9 shows a side view of FIG. 8.
Figure 10:
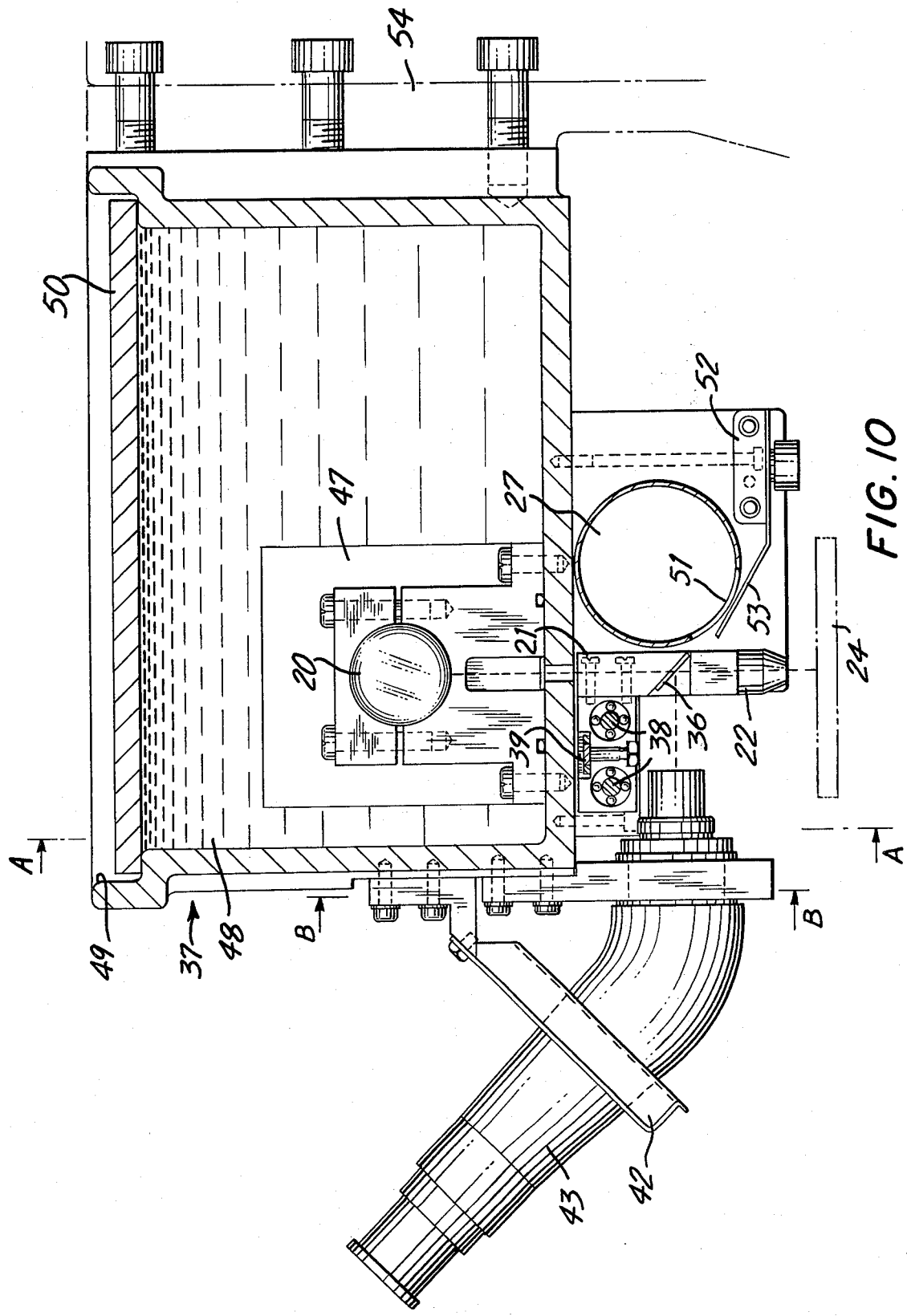
FIG. 10 shows an enlarged cross sectional view of a main part in FIG. 8.

FIGS. 8, 9 and 10 show the device equipped with the microscope 43, in which the microscope 43 is projected from a center portion of a casing 54 and a sample holder positioning means 55 is located beneath the sample holder 23. The essential portion of the sample 24 is enlarged by the microscope 43. Accordingly, the X-ray is irradiated accurately at the levelled portion since the optical axis coincide with the X-ray axis. On this occasion the microscope can adjust a sight at a small area such as about 0.3 mm$\phi$.

Referring further to another embodiment of the present invention, the mirror 36 is made of the material which reflects light transmitting the X-ray, such as an aluminium plate evaporated on a $SiO_2$ plate or an aluminium plate evaporated on an organic film. Accordingly, the X-ray is irradiated on the sample 24 through the mirror 36 and the sample 24 is visible reflected by the mirror 36.

The fluorescent X-ray film thickness gauge according to the present invention has the above noted construction and operation. The X-ray axis of the X-ray tube coincide with the optical axis of the viewing means, thereby an X-ray measuring point for sample can be observed and the X-ray measuring point can be determined from the same direction as the X-ray axis of the X-ray tube. Therefore, a small measuring area about 0.3 mm$\phi$ is measurable. The shape of the X-ray beam irradiated on the sample becomes circular, whereby the mis-irradiation and mis-measurement are completely eliminated.

I claim:

1. A fluorescent X-ray film thickness gauge comprising: an X-ray tube for irradiating an X-ray; a detector for detecting a fluorescent X-ray from a sample to which an X-ray is irradiated from the X-ray tube; a collimator for guiding the X-ray to the sample; a shutter interposed between the collimator and the X-ray tube slidably in the horizontal direction; a mirror positionable on a passing axis of the X-ray; and a viewing means for viewing a point to irradiate the X-ray on the sample; wherein an optical axis of the viewing means corresponds with the passing axis of the X-ray.

2. A fluorescent X-ray film thickness gauge according to claim 1, wherein said viewing means consists of a microscope.

3. A fluorescent X-ray film thickness gauge according to claim 1, wherein said shutter and said mirror are formed in one body.

4. A fluorescent X-ray film thickness gauge according to claim 1, wherein said mirror reflects light to pass the X-ray.

5. A fluorescent X-ray film thickness gauge according to claim 1, wherein said detector is provided with filter plate made of cobalt at an opening thereof.

* * * * *